(12) United States Patent
Kai et al.

(10) Patent No.: US 9,149,587 B2
(45) Date of Patent: Oct. 6, 2015

(54) SPRAYER

(71) Applicant: TERUMO KABUSHIKI KAISHA, Tokyo (JP)

(72) Inventors: Miho Kai, Kanagawa (JP); Kenji Yokoyama, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 13/967,092

(22) Filed: Aug. 14, 2013

(65) Prior Publication Data

US 2013/0331658 A1    Dec. 12, 2013

Related U.S. Application Data

(63) Continuation of application No. PCT/JP2012/050047, filed on Jan. 5, 2012.

(30) Foreign Application Priority Data

Feb. 25, 2011  (JP) .................................. 2011-039160

(51) Int. Cl.
*A61B 1/00*   (2006.01)
*A61B 1/06*   (2006.01)
(Continued)

(52) U.S. Cl.
CPC .......... *A61M 11/06* (2013.01); *A61B 17/00234* (2013.01); *A61B 17/00491* (2013.01); *A61B 19/5202* (2013.01); *A61B 2017/0084* (2013.01); *A61B 2017/00331* (2013.01);
(Continued)

(58) Field of Classification Search
CPC .......... A61B 17/0049; A61B 19/5202; A61B 2017/00495; A61B 2017/00544; A61M 37/00; A61M 11/06
USPC .................................................. 600/247–249
See application file for complete search history.

(56) References Cited

U.S. PATENT DOCUMENTS 5,612,050 A    3/1997 Rowe et al.
5,800,373 A    9/1998 Melanson et al.
(Continued)

FOREIGN PATENT DOCUMENTS

JP    2001-25467 A    1/2001
JP    2003-250806 A   9/2003
(Continued)

OTHER PUBLICATIONS

International Search Report (PCT/ISA/210) issued on Apr. 17, 2012, by the Japanese Patent Office as the International Searching Authority for International Application No. PCT/JP2012/050047.
(Continued)

*Primary Examiner* — Sameh Boles
(74) *Attorney, Agent, or Firm* — Buchanan Ingersoll & Rooney PC

(57) ABSTRACT

A sprayer includes: a sprayer body; a nozzle extending from the sprayer body; and an irradiation unit disposed on a leading end of the nozzle and emitting light that is oriented and diffuses in a leading end direction of the nozzle. The nozzle includes: an elongated nozzle body extending from the sprayer body and having a curved portion on a leading end side; and a nozzle head disposed on a leading end of the nozzle body. The irradiation unit is arranged inside a curve shape of the curved portion.

12 Claims, 7 Drawing Sheets

(51) Int. Cl.
  *A61M 11/06* (2006.01)
  *A61B 17/00* (2006.01)
  *A61M 37/00* (2006.01)
  *A61B 17/29* (2006.01)
  *A61B 19/00* (2006.01)
  *B05B 7/04* (2006.01)
  *B05B 7/24* (2006.01)

(52) U.S. Cl.
  CPC ............... *A61B 2017/00495* (2013.01); *A61B 2017/00522* (2013.01); *A61B 2017/00544* (2013.01); *A61B 2017/2904* (2013.01); *A61B 2019/521* (2013.01); *A61M 37/00* (2013.01); *B05B 7/0408* (2013.01); *B05B 7/2424* (2013.01)

(56) References Cited

U.S. PATENT DOCUMENTS 5,993,378 A * 11/1999 Lemelson ............... 600/109
2008/0025671 A1   1/2008 Boutoussov et al.

FOREIGN PATENT DOCUMENTS

| JP | 2008-289617 A | 12/2008 |
| JP | 2010-233940 A | 10/2010 |
| WO | 2011/153406 A2 | 12/2011 |

OTHER PUBLICATIONS

Supplementary European Search Report issued May 28, 2015, by the European Patent Office, in corresponding European Patent Application No. 12749692.5. (7 pages).

* cited by examiner

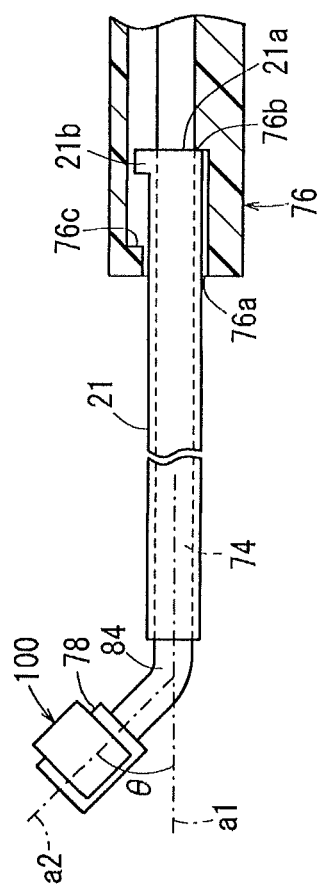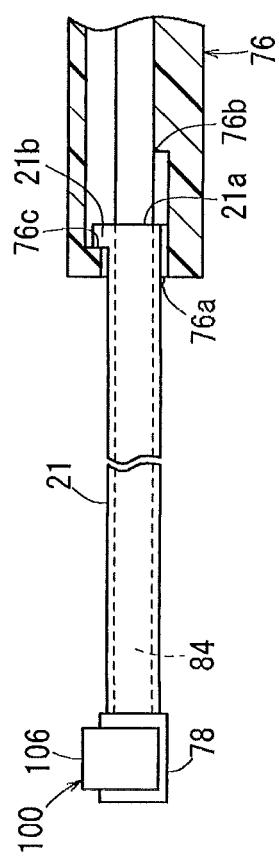
FIG. 4A
FIG. 4B

SPRAYER

CROSS REFERENCES TO RELATED APPLICATIONS

This application is a continuation of International Application No. PCT/JP2012/050047 filed on Jan. 5, 2012, and claims priority to Japanese Application No. 2011-039160 filed on Feb. 25, 2011, the entire content of both of which is incorporated herein by reference.

TECHNICAL FIELD

The present invention generally relates to a sprayer that discharges a drug from a leading end of a nozzle and applies the discharged drug to a target site.

BACKGROUND DISCUSSION

Formation of adhesion between an incisional wound and its peripheral tissue after a laparotomy can induce various disorders. To prevent such adhesion, an anti-adhesive material is used. A sheet-like anti-adhesive material is attached below an incisional wound. However, since the tissue below an incisional wound moves, the incisional wound and the tissue cannot be surely isolated. Also, it is difficult to attach the anti-adhesive material over the incisional wound after a laparotomy.

There is a known method of applying a liquid anti-adhesive material using a sprayer in which an incised portion is sutured while leaving a part of the incised portion as an opening, and a nozzle of the sprayer is inserted from the opening. An example of this method is described in Japanese Application Publication No. 2008-289617. However, in the case of a laparotomy, the direction of a nozzle and the distance from the nozzle to a target site cannot be directly viewed, and whether or not the anti-adhesive material is sprayed toward the incisional wound is not known. In the case of a laparoscopic surgery, the direction of a nozzle and the distance from the nozzle to a target site is difficult to be known using a monitor. Therefore, uneven spraying and increased use of a drug are caused.

SUMMARY

A sprayer that discharges a drug and applies the discharged drug to a target site, includes: a sprayer body; a nozzle that extends from the sprayer body; and an irradiation unit disposed at a leading end of the nozzle and emitting light that is oriented and diffuses in a leading end direction of the nozzle.

Diffused light is irradiated in a direction oriented by the nozzle by the irradiation unit disposed to the leading end of the nozzle. Therefore, a direction of the leading end of the nozzle and an approximate distance to an irradiated site can be predicted based on a position irradiated by the light and a size of the irradiated site. Thus, the drug can be applied to an exact site.

The nozzle includes: an elongated nozzle body extending from the sprayer body and having a curved portion on a leading end side thereof; and a nozzle head disposed on the leading end of the nozzle body. The irradiation unit may be placed inside the curve shape of the curved portion.

Thus, when a drug is discharged while the nozzle is directed upward, the irradiation unit is placed on the opposite side to a side where the drug is likely to drop from the leading end of the nozzle. Accordingly, the drug is unlikely to attach to the irradiation unit. Therefore, the irradiation unit can surely irradiate light in a direction oriented by the leading end of the nozzle. Also, the position oriented by the leading end of the nozzle can be easily aligned with an incisional wound or a wound.

The nozzle may be configured to spray a drug so that a diffusion diameter of the drug discharged from the nozzle and a diffusion diameter of the light emitted from the irradiation unit are substantially the same.

Accordingly, a diffusion range (a size) of the irradiated light and a spray range by discharge of a drug become approximately the same. Thus, the spray range of a drug can be predicted based on a size of the diffusion diameter of the light. Therefore, a drug can be easily applied to a desired range.

The irradiation unit may include a light source. Furthermore, a conductive member that conducts an electric current from a power source unit to the light source may be arranged along the nozzle. Also, in this case, in the above-described sprayer, the nozzle may include: an elongated nozzle body extending from the sprayer body and having an elastic curved portion on a leading end side thereof; and a nozzle head disposed on the leading end of the nozzle body. The sprayer may further include a shape regulating member being movably disposed along a longitudinal direction of the nozzle body and changing a shape of the curved portion depending on the longitudinal position. The conductive member may be arranged to extend through an inside of the shape regulating member.

Thus, by providing a light source on a leading end of a nozzle and conducting an electric current to the light source via a conductive member, a structure of irradiating light in a leading end direction of the nozzle can be provided at relatively low cost. Also, since the conductive member is covered by a shape regulating member, the conductive member can be rather easily and compactly wired along the nozzle.

The irradiation unit may be constructed to include a lens that diffuses light, and a light-guiding member that guides light from the light source to the lens may be arranged along the nozzle. Also, in this case, the nozzle may include: an elongated nozzle body extending from the sprayer body and having an elastic curved portion on a leading end side thereof; and a nozzle head disposed on the leading end of the nozzle body. The sprayer may further include a shape regulating member being movably disposed along a longitudinal direction of the nozzle body and changing a shape of the curved portion depending on the longitudinal position. The conductive member may be arranged to extent through the inside of the shape regulating member.

Thus, by providing the lens on the leading end of the nozzle and guiding light to the lens via the light-guiding member, the leading end of the nozzle can be structured in a relatively compact manner. Also, since the light-guiding member is covered by the shape regulating member, the light-guiding member can be rather easily wired along the nozzle.

According to another aspect, a sprayer that discharges a drug and applies the discharged drug to a target site includes: a syringe comprised of a cylinder and a plunger, with the cylinder possessing an interior containing a liquid constituting at least a component of the drug to be applied to the target site, and the plunger being movably positioned in the interior of the cylinder to discharge the liquid out of the interior of the cylinder; an elongated nozzle body extending in a forward direction relative to the syringe, and a nozzle head at a forward end of the elongated nozzle body. The nozzle head includes a joining channel in communication with the interior of the cylinder so that the joining chamber receives the liquid from the cylinder when the plunger is moved in the forward direction in the cylinder. The joining channel also receives gas which mixes with the liquid in the joining chamber to atomize the liquid. The nozzle head also includes a discharge port in communication with the joining chamber and through which the atomized liquid is ejected from the sprayer to be applied to the target site. The sprayer also includes an irradiation unit disposed on a leading end of the nozzle head to emit light that is oriented toward, and diffuses in, a leading end direction of the nozzle head.

According to a further aspect, a method of applying a drug to a target site in a living body involves: inserting a leading end of a nozzle into a living body, wherein the nozzle includes a drug discharge port from which the drug is discharged and an irradiation unit that emits light that diffuses in a direction away from the nozzle; irradiating tissue in the living body by directing the diffused light from the irradiation unit at the tissue; adjusting a position of the nozzle so that an irradiated site of the tissue that is irradiated by the diffused light is aligned with the target site; and discharging the drug from the nozzle at the target site to apply the drug to the target site.

BRIEF DESCRIPTION OF DRAWINGS

FIG. 4A is a schematic view of the sprayer with the curved portion of the nozzle being curved, and FIG. 4B is a schematic view of the sprayer with the curved portion of the nozzle being regulated linearly.

DETAILED DESCRIPTION

Figure 1:
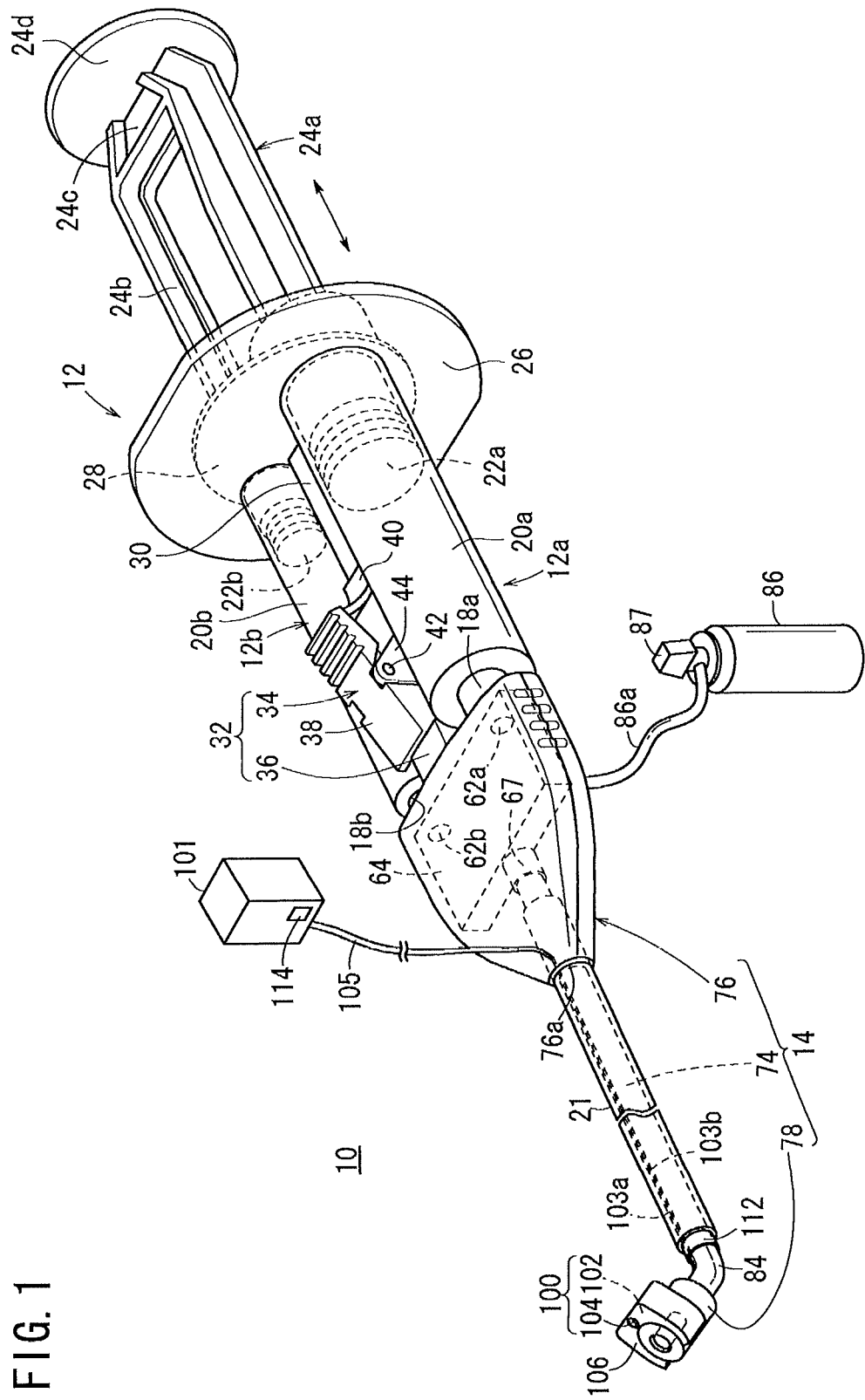
FIG. 1 is a partially omitted perspective view of a sprayer according to an embodiment disclosed here.

Preferred embodiments of a sprayer disclosed here will be described below, and explained with reference to the accompanying drawings. Referring to FIG. 1, the sprayer 10 is configured to apply or spray two types of liquids each having a different composition (hereinafter, the two types of liquids will be referred to as a "first liquid" and a "second liquid" for the convenience of explanation) while mixing the two liquids. The sprayer 10 is a spray device including a syringe (a sprayer body) 12 having a first syringe (a supply unit) 12a and a second syringe (a supply unit) 12b arranged in parallel and integrally linked together, and a nozzle 14 connected to the leading end of each of the syringes 12a, 12b forming the syringe 12 thereby to spray the first liquid and the second liquid filled in the syringe 12 toward an application target.

The sprayer 10 is used, for example, as a medical device configured to spray a solution of a drug, comprised of a mixture of the first and second liquids, to an organ, an abdominal wall and the like, while mixing (in the nozzle 14) the first and second liquids having different liquid compositions which are supplied from the syringe 12, while the nozzle 14 is inserted in an abdominal cavity during a laparoscopic surgery.

The syringe 12 includes the first syringe 12a and the second syringe 12b corresponding to or containing the two types of liquids to be mixed in the nozzle 14 and sprayed. The syringe 12 is used by filling liquid in the first syringe 12a and filling liquid in the second syringe 12b. In the present embodiment, the first syringe 12a and the second syringe 12b have a substantially similar structure except that the first and second syringes 12a and 12b have different outer diameters and volumes. Therefore, the first syringe 12a will be described below by way of example, with features of the first syringe designated by the addition of "a" to the reference number. A detailed explanation of the same features present in the second syringe 12b will not be omitted, but the features in the second syringe that are the same as and correspond to features in the first syringe are identified by the addition of "b" instead of "a". Though it was mentioned that the first and second syringes possess different diameters, it is possible that the first syringe 12a and the second syringe 12b may be configured to have the same diameter.

The first syringe 12a includes an outer cylinder (cylinder) 20a having a reduced-diameter communication port (discharge port) 18a disposed at the leading end (distal end) of the cylinder, a gasket 22a configured to slide in a liquid-tight manner in the outer cylinder 20a, and a plunger (plunger rod) 24a for moving the gasket 22a in an axial direction of the outer cylinder 20a. The communication port 18a is an opening for communicating liquid inside and outside the outer cylinder 20a, and a tapered convex portion projecting from a leading end surface of the outer cylinder 20a.

An elliptical sheet-like flange 26, on which an index finger, a middle finger or the like is placed when an operator manipulates the plunger 24a, is positioned around the base end outer periphery of the outer cylinder 20a. The flange 26 is formed integrally with the base end outer periphery of an outer cylinder 20b of the second syringe 12b. A guide member 28 is inserted and fitted in the base end-side openings of the outer cylinders 20a and 20b. The guide member 28 is configured to guide forward and backward movements of the plungers 24a and 24b. A scale for indicating an amount of liquid may be provided on the outer peripheral surface of the outer cylinder 20a (20b).

Examples of materials from which the outer cylinder 20a (20b) cab be fabricated include, but are not limited to, a resin including polyvinyl chloride, polyethylene, polypropylene, cyclic polyolefin, polystyrene, poly(4-methylpentene-1), polycarbonate, an acrylic resin, an acrylonitrile-butadiene-styrene copolymer, polyester such as polyethylene terephthalate and polyethylene naphthalate, a butadiene-styrene copolymer, and polyamide (e.g., nylon 6, nylon 6/6, nylon 6/10, nylon 12). However, in view of easiness of formation, low water vapor permeability, and the like, polypropylene, cyclic polyolefin, polyester, and the like are preferred. The outer cylinder 20a is preferably transparent or translucent in order to ensure visibility of the interior of the outer cylinder.

The plunger 24a is an elongated rod having an axially orthogonal cross-section configured in a cross shape, and inserted through a cross-shaped guide hole axially extending through the first syringe 12a side of the guide member 28. Similarly, the plunger 24b is inserted through a cross-shaped guide hole axially extending through the second syringe 12b side of the guide member 28.

The plungers 24a and 24b are integrally linked to each other on the base end sides of the two plungers via a bridge 24c, and are configured to possesses an overall general U-shape. That is, the forward and backward movements of the plungers 24a and 24b are integrated by a common manipulation unit (a manipulation circular plate) 24d disposed at or connected to the bridge 24c. The material of the plunger 24a (24b) may be similar to that of the above-described outer cylinder 20a. However, the material is desirably non-transparent in order to improve visibility in the transparent outer cylinder 20a The gasket 22a is a piston made of, for example, an elastic material and connected to a leading end of the plunger 24a to tightly engage and slide along the inner peripheral surface of the outer cylinder 20a so that the gasket 22a slides in the outer cylinder in a liquid-tight manner. The gasket 22a can suck liquid from the communication port 18a into a chamber formed on a leading end side of the gasket 22a, and can also push out the filled liquid from the communication port 18a.

The material forming the gasket 22a (22b) is not particularly limited, and examples include elastic materials including various rubber materials such as natural rubber, butyl rubber, isoprene rubber, butadiene rubber, styrene-butadiene rubber, and silicone rubber; various thermoplastic elastomers such as polyurethane-based, polyester-based, polyamide-based, olefin-based, and styrene-based; or mixtures thereof may be used.

The second syringe 12b has a substantially similar structure to the above-described first syringe 12a, and includes a communication port 18b, an outer cylinder 20b, a gasket 22b, and a plunger 24b with the flange 26 and the guide member 28 shared with the first syringe 12a.

The first syringe 12a and the second syringe 12b are linked to each other by the flange 26 on the base end side. The portions extending from the centers to the leading ends of the first and second syringes 12a and 12b are connected by a flat plate-shaped linking unit 30. A hook member 34 is disposed on the linking unit 30. The hook member 34 constitutes an engagement mechanism (a lock mechanism) 32 for locking or unlocking the syringe 12 and the nozzle 14 when attaching or detaching the nozzle 14 to or from the syringe 12. The engagement mechanism 32 has the hook member 34 and a pawl member 36. The pawl member 36 is positioned on the nozzle 14 side and is configured to be engaged by the hook member 34.

The hook member 34 includes a body part 38 and a sheet-shaped elastic piece (an elastic body) 40 extending downward from a base end of the body part 38. Pins 42 and 42 projecting from both sides in a width direction of the body part 38 are pivotally supported with respect to a pair of support members 44 and 44. Thus, the body part 38 is configured to swing. The elastic piece 40 curves toward an inner side, and its end lands on the linking unit 30. The elastic piece 40 is also a leaf spring-like member configured to slide on the linking unit 30, and is biased in a direction of swinging a leading end of the body part downward around the pins 42 as a rotation axis.

In such a syringe 12, a first liquid to be filled in the first syringe 12a and a second liquid filled in the second syringe 12b may be appropriately selected depending on the application and the intended purpose of the sprayer 10. For example, when used for administration of an adhesive for a living body tissue, liquid (a solution or the like) containing thrombin may be used as one of the first and second liquids, and liquid (a solution or the like) containing fibrinogen may be used as the other. Also, for example, when the sprayer 10 is used for administration of an anti-adhesive material, liquid (a solution or the like) containing carboxymethyl dextrin modified with a succinimidyl group may be used as one of the first and second liquids, and liquid (a solution or the like) containing disodium hydrogen phosphate may be used as the other.

When such a combination of the first liquid and the second liquid is mixed, the liquids are changed in properties, that is, gelled (hardened). By gelation, for example, a drug solution (a mixture or mixed liquid) provided by mixing two liquids can be surely retained in the living body tissue with the drug solution applied, so that a function as an adhesive for a living body tissue or an anti-adhesive material can surely be exerted in the target site. Of course, the type and the combination of the first liquid and the second liquid are not limited to the above-described examples.

A cylinder 86, which is depicted as a structural example of a gas supply source, contains a high pressure (compressed) sterile gas (hereinafter, merely referred to as a "gas") filled in an interior space, and is configured to supply (transfer) the gas to the sprayer 10 (the nozzle 14). As the gas, for example, carbon dioxide may be used. The cylinder 86 includes a valve (a cock) 87 that is capable of opening and closing and controls supply and termination of supply of gas to the sprayer 10. When the sprayer 10 is used, the valve 87 is placed in an open state.

The nozzle 14 includes an elongated nozzle body 74, a nozzle support unit (housing) 76 for supporting a base end of the nozzle body 74, and a nozzle head 78 disposed on a leading end of the nozzle body 74. The nozzle support unit 76 is made of, for example, a metal material or a resin material, and has a block-like outer shape.

The nozzle support unit 76 is a member made of, for example, a metal material or a resin material, and has a planar view of a tapered and generally triangular shape. The nozzle support unit 76 is also a box-shaped member having a circular opening 76a at a leading end of the box-shaped member and a rectangular opening at a base end of the box-shaped member. The nozzle body 74 is inserted through (passes through) the opening 76a, and a flow channel member 64 faces the rectangular opening in an advanceable and retractable manner.

The flow channel member 64 capable of advancing and retreating in the back-and-forth direction is arranged inside the nozzle support unit 76. Connection ports 62a and 62b are formed on a base end surface of the flow channel member 64. The connection ports 62a and 62b are engaged by the communication ports 18a and 18b of the syringe 12 respectively. An outlet port 67 projects from the leading end surface of the flow channel member 64, and a gas port is disposed on a bottom surface. The base end of the nozzle body 74 is inserted into and connected to the outlet port 67, and a tube 86a from the cylinder 86 is inserted into and connected to the gas port.

Inside the nozzle body 74, there are disposed a first nozzle liquid flow channel through which the first liquid supplied from the first syringe 12a flows, a second nozzle liquid flow channel through which the second liquid supplied from the second syringe 12b flows, and a nozzle gas flow channel through which the gas supplied from the cylinder 86 flows.

The first and second nozzle liquid flow channels extend to the leading end direction in the nozzle body 74, and are thereafter joined with each other in a joining channel 58 (see FIG. 2) arranged in the nozzle head 78. The leading ends of the nozzle liquid channels are integrally joined with each other on the base end of the joining channel 58, so that both liquids can be substantially uniformly and surely mixed.

Figure 2:
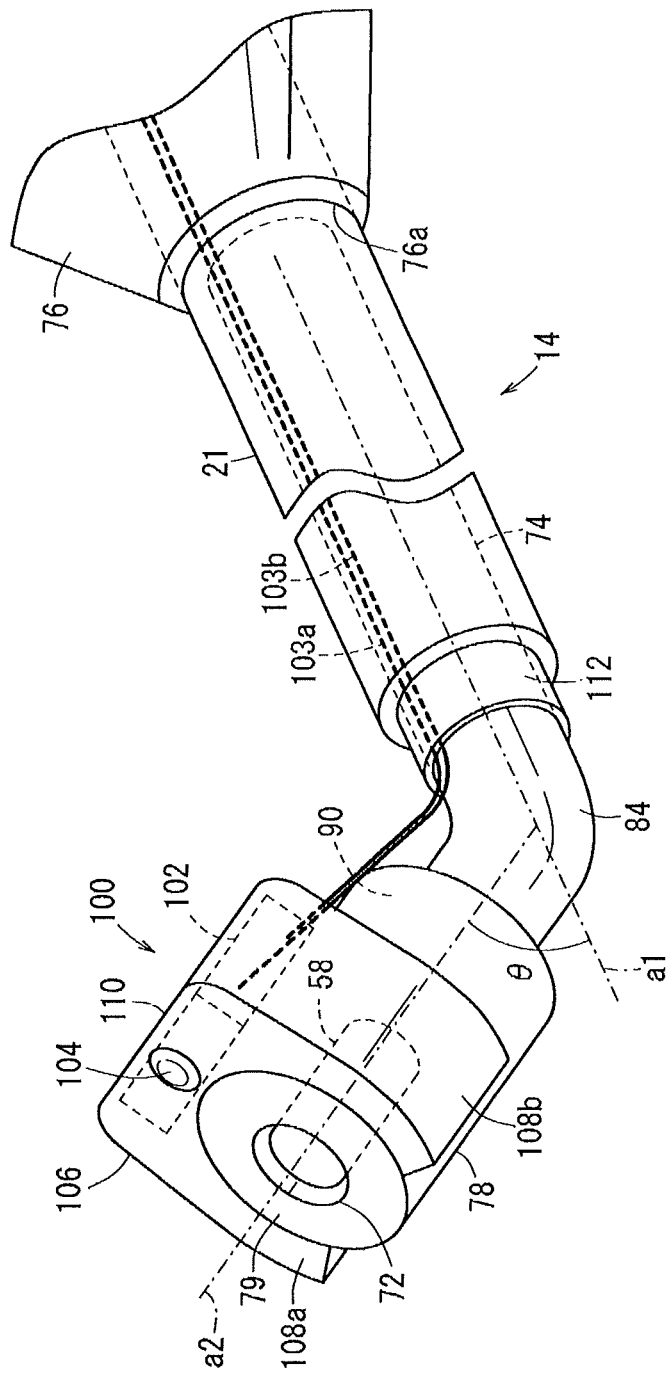
FIG. 2 is a partially omitted perspective view of a nozzle of the sprayer depicted in FIG. 1.

As depicted in FIG. 2, the nozzle head 78 has a cylindrical outer shape, and includes a jet port or discharge port 72 having an opening on a leading end wall portion 79. The leading end of the joining channel 58 is connected to the jet port 72. The jet port 72 is an opening for discharging a mixture of the first liquid and the second liquid mixed in the joining channel 58 and the gas. The constituent material of which the nozzle head 78 can be fabricated, although not particularly limited, can include, for example, the constituent materials of the nozzle support unit 76.

The nozzle gas flow channel through which gas flows is defined by an inner cavity of the nozzle body 74 that is an outer tube connected to the outlet port 67 of the flow channel member 64. That is, the nozzle body 74 is an outer tube and is connected to the outlet port 67 of the flow channel member 64, and the interior of this outer tube constitutes the nozzle gas flow channel through which gas flows. The first and second nozzle liquid flow channels and the joining channel 58 are arranged as inner tubes inside the nozzle body (i.e., the first and second nozzle liquid flow channels and the joining channel 58 are positioned in the nozzle gas flow channel), and the joining channel 58 is provided with interstices or through holes allowing the gas in the nozzle gas flow channel to enter the joining channel 58 and mix with the first and second liquids which have been joined mixed in the joining channel 58.

Therefore, the wall surface of the joining channel 58 is made of a permeable film through which gas can pass and liquid cannot pass, and thus the gas that has flowed through the nozzle gas flow channel enters through the tube wall of the joining channel 58 into the inside of the joining channel 58. This allows the mixed liquid flowing though the joining channel 58 to be jetted out of the jet port 72 together with the gas entering from the surroundings for atomization. Thus, the mixed liquid is uniformly applied to a target site (an affected area).

As depicted in FIG. 1, the nozzle body 74 is configured as an elongated tubular body, and connects the leading end of the nozzle support unit 76 and the base end of the nozzle head 78. The nozzle body 74 has a curved portion 84 that is curved or bent and has elasticity (flexibility). The curved portion 84 is, in the present embodiment, curved or bent such that the leading end of the curved portion 84 is directed obliquely upward.

As depicted in FIG. 2, the curved portion 84 causes an axis a2 of the nozzle head 78 to be tilted with respect to an axis a1 of the nozzle body 74 (strictly speaking, an axis of a portion of the nozzle body 74 from the curved portion 84 toward the base end side). When the curved portion 84 is curved or bent without being regulated by a sheath 21, a tilt angle θ (hereinafter, referred to as a "maximum tilt angle θ MAX") of the axis a2 of the nozzle head 78 with respect to the axis a1 of the nozzle body 74 is preferably about 30 to 90°, more preferably about 45 to 70°.

The curved portion 84 of the nozzle body 74 is made of a soft material, an elastic material, and the like. The portion of the nozzle body 74 from the curved portion 84 toward the base end side may be made of a hard material, or may be made of a soft material, an elastic material, and the like to have elasticity.

The curved portion 84 and the portion of the nozzle body 74 from the curved portion 84 toward the base end side may be made of different materials and fixed together by adhesion, fusion, and the like, or may be molded as a single piece.

Examples of a constituent material of the nozzle body 74 include, but not are not particularly limited to, various soft and hard resins such as polyvinyl chloride, various rubber materials such as natural rubber and butyl rubber, various thermoplastic elastomers such as polyurethane-based and polyester-based, various metal materials such as stainless steel, aluminum, and copper or copper alloy, various glasses, and various ceramics such as alumina and silica. Any of the above materials can be used for the portion of the nozzle body 74 from the curved portion 84 toward the base end side, and a soft material or an elastic material among the above materials can be used for the curved portion 84.

As depicted in FIGS. 1 and 2, the sprayer 10 further includes the sheath (the elongated tubular body) 21 functioning as a shape regulating member for regulating the shape (or degree of curvature) of the curved portion 84 of the nozzle body 74. The nozzle body 74 is inserted through (inserted into) and positioned inside the sheath 21 (a through hole of the sheath 21), and the sheath 21 is movable with respect to the nozzle body 74 along a longitudinal direction (an axial direction) of the nozzle body 74. Although the sheath 21 may be configured so that at least curved portion 84 of the nozzle body 74 is inserted or positioned in the sheath 21, the sheath 21 in the present embodiment is configured so that the portion of the nozzle body 74 extending to the vicinity of the base end of the nozzle body 74 is inserted. That is, a portion of the nozzle body on the proximal end or base end side of the curved portion 84 is positioned in the sheath 21.

The sheath 21 is preferably made of a hard material to have a necessary and sufficient stiffness and further low sliding properties so that the shape of the curved portion 84 can be regulated. Examples of a constituent material from which the sheath 21 can be fabricated include hard resins including polyolefin resins such as polyethylene and polypropylene, various metal materials such as stainless steel, aluminum, and copper or copper alloy, various glasses, and various ceramics such as alumina and silica.

Since the sheath is configured as described above, the length of the curved portion 84 projecting from the leading end of the sheath 21 is adjusted and the shape of the curved portion 84 is changed by grasping and moving the sheath 21 in an axial direction. Thus, the tilt angle θ of the axis a2 of the nozzle head 78 with respect to the axis a1 of the nozzle body 74 can be adjusted.

The sheath 21 is configured to move between a non-regulated position (a first position) and a regulated position (a second position). In the non-regulated position, the curved portion 84 is curved or bent without being regulated by the sheath 21, and the axis a1 of the nozzle body 74 is tilted with respect to the axis a2 of the nozzle head 78. In the regulated position, the curved portion 84 is corrected (regulated) by the sheath 21 to become linear, and a direction of the axis a2 of the nozzle head 78 and a direction of the axis a1 of the nozzle body 74 are the same. That is, in the regulated position, the axis a2 of the nozzle head 78 and the axis a1 of the nozzle body 74 are coincident or coaxial.

As depicted in FIG. 4A, when the sheath 21 is placed in the non-regulated position, the entire curved portion 84 projects from the leading end of the sheath 21, and the curved portion 84 is curved or bent without being regulated by the sheath 21. At this time, an edge 21a of the sheath 21 and a stepped portion 76b of the nozzle support unit 76 abut against each other so that the sheath 21 is positioned in the non-regulated position.

For adjusting the tilt angle θ, the sheath 21 is moved forward toward the leading end direction so that the tilt angle θ gradually decreases. When the sheath 21 is moved to the regulated position, as depicted in FIG. 4B, the entire curved portion 84 is inserted or positioned in the sheath 21, and the curved portion 84 is straightened by the sheath 21 and becomes linear.

At this time, a stepped portion 76c disposed on the nozzle support unit 76 and a projection 21b disposed on the base end or the vicinity thereof of the sheath 21 abut against each other so that the sheath 21 stops and is positioned at the regulated position. When the sheath 21 is located in the regulated position, the nozzle head 78 projects from the leading end of the sheath 21.

When the sheath 21 is moved from the state depicted in FIG. 4B toward the base end direction (i.e., toward the non-regulated position), the tilt angle θ gradually increases. When the sheath 21 is moved to the first position, the entire curved portion 84 projects from the leading end of the sheath 21, and the curved portion 84 is not regulated by the sheath 21 anymore. Thus, as depicted in FIG. 4A, the curved portion 84 is in a state of being curved or bent.

The adjustment of the tilt angle θ may be performed concurrently at the time of a manipulation of discharging (ejecting) a first liquid and a second liquid, after the manipulation of ejecting a first liquid and a second liquid, or before the manipulation of ejecting a first liquid and a second liquid. Also, the adjustment of the tilt angle θ may be previously performed, and then the manipulation of ejecting a first liquid and a second liquid may be initiated, followed by further manipulation of adjusting the tilt angle θ.

When using the sprayer 10 configured as described above, the first liquid in the first syringe 12a and the second liquid in the second syringe 12b are supplied into the nozzle body 74 via the flow channel member 64 by forwardly pushing the manipulation unit 24d toward the flange 26 while placing fingers (for example, an index finger and a middle finger) on both left and right sides of the flange 26 and another finger (for example, a thumb) on the manipulation unit. Then, the first liquid and the second liquid are mixed with the gas supplied from the cylinder 86 in the joining channel 58 to be jetted from the jet port 72 disposed on the leading end of the nozzle 14 for atomization. Thus, the mixture is uniformly applied to the target site.

Figure 3:
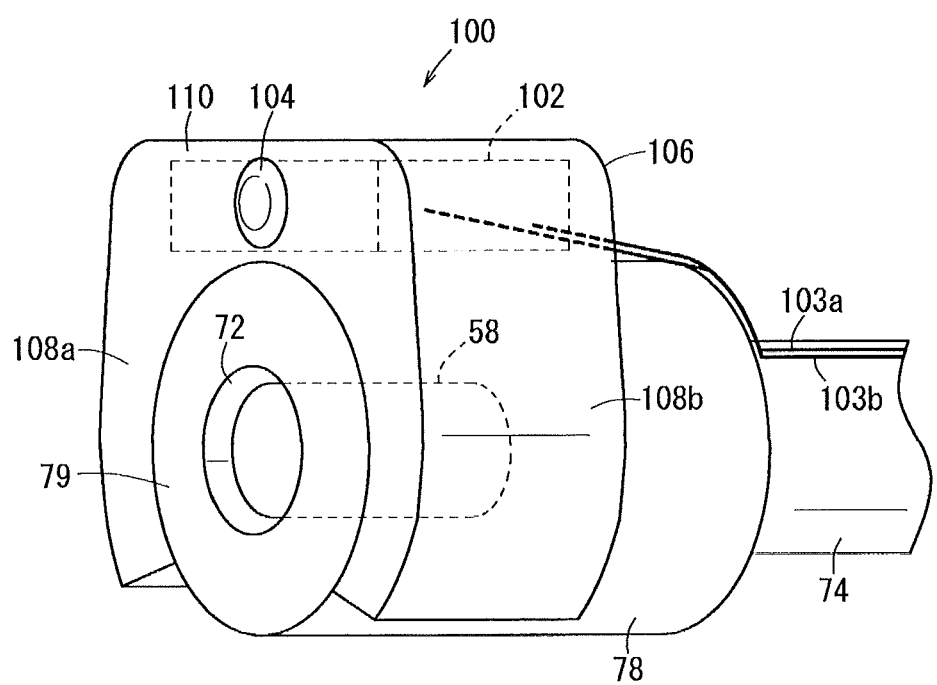
FIG. 3 is a partially omitted perspective view of the leading end portion of the nozzle of the sprayer depicted in FIG. 1.

The sprayer 10 according to the present embodiment further includes, as depicted in FIGS. 1 to 3, an irradiation unit 100 disposed on the leading end of the nozzle 14 and emitting light that is oriented and diffuses in the leading end direction of the nozzle 14, a power source unit 101 supplying electric power to the irradiation unit 100, and lead wires (conductive members) 103a and 103b connected to the power source unit 101 to lead electric current from the power source unit 101 to a light source 102.

The irradiation unit 100 is disposed on the leading end (the nozzle head 78) of the nozzle 14, and has the light source 102 generating illumination light and a lens 104 transforming light from the light source 102 into circular diffused light oriented in the leading end direction of the nozzle 14. According to such a structure, diffused light is irradiated by the irradiation unit 100 disposed on the leading end of the nozzle 14 in the direction oriented by the nozzle 14. That is, light is irradiated toward the target site at which to apply a drug (a drug solution).

As depicted in FIGS. 1 and 2, in the present embodiment, the irradiation unit 100 is positioned on the inside of the curved shape of the curved portion 84 on the leading end of the nozzle 14. This allows the lens 104 constituting the most leading end of the irradiation unit 100 to be positioned higher than the leading end of the nozzle 14.

As the light source 102, a light emitting diode (LED), a semiconductor laser (LD), an electric bulb, and the like can be used. The light emitting diode and the semiconductor laser, which can be structured so as to be relatively small and light, are preferred as the light source 102 disposed on the nozzle head 78 which is desired to be small.

The color of light generated by the light source 102 is not particularly limited as long as the color is visible light. Examples of the color include white or light pink. When the light generated by the light source 102 is light having a color opposite to that of an organ, such as bluish or greenish, the light irradiated on the target site is relatively easily seen, and distinction from the applied (sprayed) drug (for example, an anti-adhesive material) is rather easily made.

The light source 102 and the lens 104 are held by a holding member 106 to be fixed to the nozzle head 78. As depicted in FIG. 2, the holding member 106 has a pair of arm portions 108a and 108b extending in opposed relation to each other and a linking portion 110 linking the arm portions 108a and 108b. The holding member 106 is a member having a substantially U-shape as a whole. The nozzle head 78 is elastically sandwiched from both sides by the pair of arm portions 108a and 108b so that the holding member 106 is fixed with respect to the nozzle head 78. The light source 102 and the lens 104 are disposed on the linking portion 110.

Instead of independently providing the holding member 106 as described above, the nozzle head 78 may be configured to hold the light source 102 and the lens 104 by the nozzle head 78 itself.

The lead wires 103a and 103b are electrically connected to the light source 102 and the power source unit 101, and are positioned inside of the sheath 21 along the nozzle body 74. That is, at least part of the lead wires 103a and 103b are covered and protected by the sheath 21. Also, as depicted in FIGS. 1 and 2, the nozzle body 74 and the lead wires 103a and 103b may be covered together by a tubular covering member 112, and the nozzle body 74 covered by the covering member 112 as described above may be inserted through the sheath 21. The covering member 112 can be disposed from the vicinity of the curved portion 84 to the vicinity of the base end of the nozzle body 74, and constructed as, for example, a heat shrinkable tube.

The lead wires 103a and 103b pass through the wall portion of the nozzle support unit 76, extend outside the nozzle support unit 76 in a form of a single cable 105, and are electrically connected to the power source unit 101. The power source unit 101 is, for example, a battery box that houses a battery, and provided with a switch 114 that switches on/off of the power source unit 101. When the switch 114 is manipulated to turn on the power source of the power source unit 101, electric current is supplied to the light source 102 via the lead wires 103a and 103b, causing the light source 102 to emit light.

The cable 105 has a length sufficient to allow a user to use the sprayer 10 without difficulties even when the user holds the nozzle 14 and the syringe 12 with the power source unit 101 kept in a storage portion (a pocket or the like) attached to the user's clothes or hooked on the user's clothes.

Thus, since the power source unit 101 is configured to be separated from the nozzle 14 and the syringe 12, the user does not need to hold the weight including that of the power source unit 101 when using the sprayer 10, allowing the sprayer 10 to be convenient. Instead of providing the power source unit 101, an adapter capable of connecting with an external power source may be provided so that electric power is supplied from the external power source to the light source 102.

Next, an application method of an anti-adhesive material to a target site by using the sprayer 10 including the above-described irradiation unit 100 will be described.

As a first example of an application method using the embodiment of the sprayer disclosed here by way of example, a procedure is described involving applying an anti-adhesive material to a suture portion 122 (an incisional wound) of a peritoneum 120 from inside the peritoneum 120 during a laparotomy.

Figure 5:
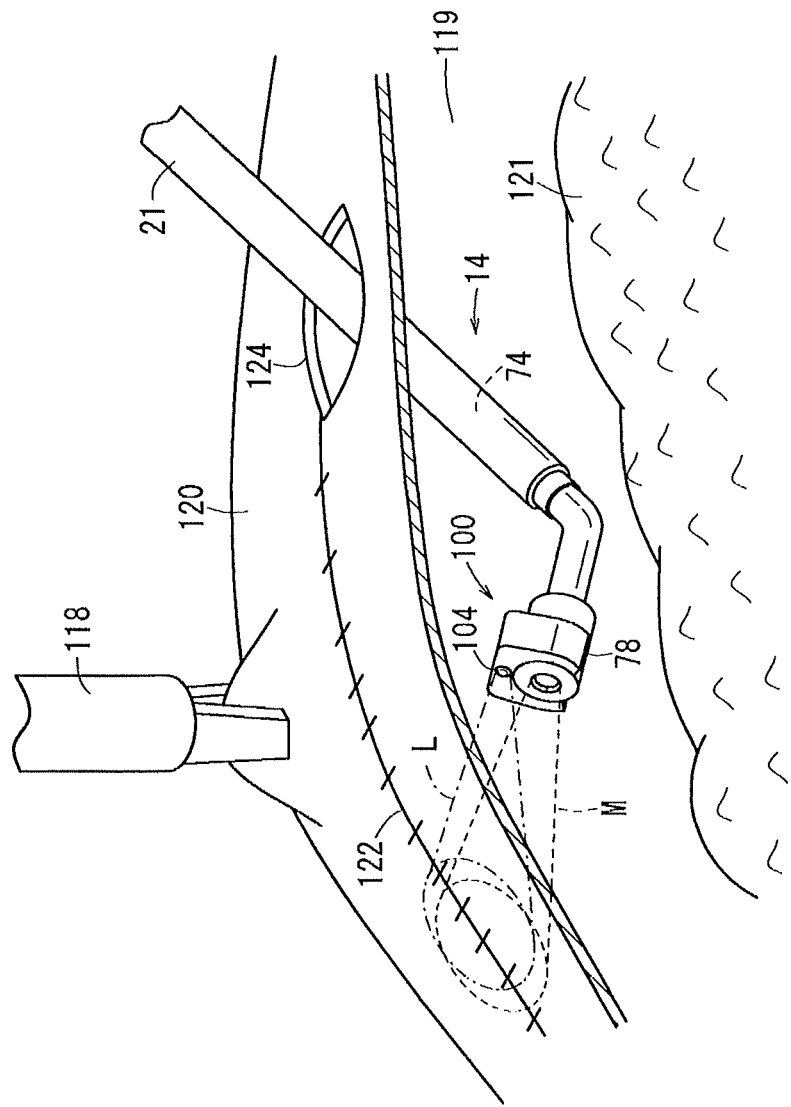
FIG. 5 is a schematic illustrative view of a maneuver or manner of operation using the sprayer depicted in FIG. 1.

As shown in FIG. 5, when suturing the peritoneum 120, a 2 to 3 cm length part of an incised portion is left without being sutured to form an opening 124 for inserting the nozzle 14.

Next, the peritoneum 120 is held by a holding means (for example, a forceps or a gripper) 118, and the peritoneum 120 is held up so that the peritoneum 120 and an organ 121 do not contact each other. Then, the power source unit 101 is manipulated to cause the light source 102 of the irradiation unit 100 to emit light, and the nozzle 14 of the sprayer 10 is inserted into an abdominal cavity 119. Thereafter, the nozzle 14 is placed in a position where a suture starting position is irradiated with light from the irradiation unit 100.

In this case, since the nozzle 14 has been inserted in the abdominal cavity 119, the leading end (the nozzle head 78) of the nozzle 14 cannot be directly viewed. However, since the peritoneum 120 is relatively thin, a part of the light from the irradiation unit 100 transmits through the peritoneum 120. For this reason, the irradiated portion can be visually recognized from the outside. Furthermore, as described above, since the light from the irradiation unit 100 is irradiated in a direction oriented by the nozzle 14, a direction irradiated by the irradiation unit 100 and a direction of discharging an anti-adhesive material from the nozzle 14 are substantially the same. Therefore, a direction of the leading end of the nozzle 14 can be predicted based on the irradiated site visually recognized from the outside.

Also, since both diffused light (hereinafter, described by affixing a sign L to "diffused light" when referring to FIG. 5) emitted from the irradiation unit 100 and anti-adhesive material (hereinafter, described by affixing a sign M to an "anti-adhesive material" when referring to FIG. 5) discharged from the nozzle 14 have a shape of widening toward the end, a widening degree of the diffused light L and a widening degree of the discharged anti-adhesive material M may be substantially the same. That is, the nozzle 14 (specifically, the nozzle head 78) and the irradiation unit 100 may be configured so that a diffusion diameter of the anti-adhesive material M discharged from the nozzle 14 and a diffusion diameter of the diffused light L emitted from the irradiation unit 100 are substantially the same.

For example, when the anti-adhesive material M discharged from the nozzle 14 has a diameter of 2.5 cm at a discharge distance of 2 cm, and a diameter of 3 to 3.5 cm at a discharge distance of 5 cm, the irradiation unit 100 is correspondingly configured so that the emitted light has a diameter of 2.5 cm at an irradiation distance of 2 cm, and a diameter of 3 to 3.5 cm at an irradiation distance of 5 cm. By configuring as described above, the distance from the irradiated site to the leading end of the nozzle 14 can be predicted based on the size (the diameter) of the irradiated site.

Therefore, the position and the direction of the nozzle 14 are adjusted by checking the position and the size of the irradiated site from the outside, so that the irradiated site reaches the target site and the size of the irradiated site becomes a desired spray diameter (for example, 2.5 to 3.5 cm). After such an adjustment, the manipulation unit 24d is pressed toward the leading end side to discharge the anti-adhesive material M from the leading end of the nozzle 14. This enables the anti-adhesive material M to be applied to an exact site. Also, since the spray range of the anti-adhesive material M can be relatively precisely predicted based on the size of the diffusion diameter of light, the anti-adhesive material M can be rather easily applied to a desired range.

Once application of the anti-adhesive material M is initiated as described above, the position of the nozzle 14 is adjusted so that the irradiated site moves along the suture portion 122 toward the opening 124 side while maintaining the size of the irradiated site, thereby to continue to apply the anti-adhesive material M. In the present embodiment, since the irradiation unit 100 is placed inside a curve shape of the curved portion 84 as described above, when the anti-adhesive material M is discharged with the nozzle 14 directed upward, the irradiation unit 100 is placed on the opposite side to a side where the anti-adhesive material M is likely to drop from the leading end of the nozzle 14. Accordingly, the anti-adhesive material M is unlikely to attach to and interfere with the irradiation unit 100. Therefore, the irradiation unit 100 (in particular, the lens 104) is not blocked by the anti-adhesive material M, and the irradiation unit 100 can relatively reliably irradiate light in a direction oriented by the leading end of the nozzle 14.

Furthermore, in a case of placing the irradiation unit 100 inside a curve shape of the curved portion 84 as in the present embodiment, when the nozzle 14 is placed so that the nozzle head 78 is tilted upward, the irradiation unit 100 is positioned on an axis of the nozzle 14 when viewed from the upper side. Therefore, the position oriented by the leading end of the nozzle 14 is relatively easily aligned with the position of the suture portion 122, so that the anti-adhesive material M can be more precisely applied to a desired target position.

When the anti-adhesive material M has been applied on the suture portion 122 to the terminal (i.e., a site close to the opening 124) as described above, the nozzle 14 is removed from the abdominal cavity 119, and the peritoneum 120 is lowered. The remaining portion (the opening 124) is sutured, and the surgery is completed.

As understood from the above description, the sprayer 10 disclosed here allows a first application method as described below to be implemented. That is, the first application method is a method of discharging a drug (an anti-adhesive material M) and applying the discharged drug to a target site, including: inserting a leading end of a nozzle 14 of a sprayer 10 into a space (an abdominal cavity 119) between an organ 121 and a membranous tissue (a peritoneum 120) through a hole (an opening 124) formed in the membranous tissue covering the organ 121 of a living body; irradiating, to the membranous tissue, diffused light L that is oriented and diffuses in a leading end direction of the nozzle 14, from a back side of the membranous tissue; adjusting a position and a direction of the nozzle 14 so that the irradiated site of the diffused light L to the membranous tissue is aligned with an application target site; and discharging the drug from the leading end of the nozzle 14.

Next, as a second example of an application method using the sprayer disclosed here, a procedure will be described involving applying an anti-adhesive material to a wound in a laparoscopic surgery.

After a predetermined surgical treatment (for example, incision, ablation, cauterization and suture) has been performed to an affected area (a living body tissue) under a laparoscope, and cleaning and hemostasis of the wound has been finished, the power source unit 101 is manipulated to cause the light source 102 of the irradiation unit 100 to emit light, and the nozzle 14 is inserted into an abdominal cavity.

Next, the position and the direction of the nozzle 14 are adjusted while checking the application target position (the affected area) through the laparoscope (the camera), so that the size (the diameter) of the irradiated site becomes a desired spray diameter (for example, 2.5 to 3.5 cm).

After such an adjustment, the manipulation unit 24d is pressed toward the leading end side to discharge (spray) the anti-adhesive material M from the leading end of the nozzle 14. This enables the anti-adhesive material to be applied to an exact site. Also, since the spray range of the anti-adhesive material can be relatively precisely predicted based on the size of the diffusion diameter of the light, the anti-adhesive material can be rather easily applied to the desired range.

When the target site has been confirmed to turn to the color of the anti-adhesive material (for example, white when the anti-adhesive material is white), the discharging of the anti-adhesive material is terminated. Then, a pneumoperitoneum is completed in the usual manner to finish the surgery.

Using the sprayer 10 disclosed here, a second application method as described below can also be implemented. The second application method is a method of discharging a drug (an anti-adhesive material M) and applying the discharged drug to a target site, including: inserting a leading end of a nozzle 14 of a sprayer 10 into an abdominal cavity 119 of a living body through a hole in an abdominal wall of the living body; irradiating, to a living body tissue in the abdominal cavity 119, diffused light L that is oriented and diffuses in a leading end direction of the nozzle 14; adjusting a position and a direction of the nozzle 14 while checking the inside of the abdominal cavity 119 through a laparoscope so that an irradiated site of the diffused light L to the living body tissue is aligned with the application target site; and discharging the drug from the leading end of the nozzle 14.

As described above, according to the sprayer 10 of the present embodiment, since the irradiation unit 100 emitting light that widens (diverges) toward the end (in a direction away from the nozzle) is provided at the leading end of the nozzle 14, the direction of the leading end of the nozzle 14 and the distance to the object can be known based on the position and the size (the diameter) of the light in the irradiated site. This allows the anti-adhesive material to be applied to a relatively exact site.

Also, in the present embodiment, the light source 102 is provided at the leading end of the nozzle 14, and electric current is conducted to the light source 102 via the lead wires 103*a* and 103*b* arranged along the nozzle body 74. Therefore, the structure which permits light to be irradiated in the leading end direction of the nozzle 14 can be provided at relatively low cost.

Furthermore, since the irradiation unit 100 is placed inside a curve shape of the curved portion 84, the anti-adhesive material M is inhibited from attaching to the irradiation unit 100, and the position oriented by the leading end of the nozzle 14 can be relatively easily aligned with the suture portion 122 (an incisional wound) or a wound.

Still furthermore, in the present embodiment, the lead wires 103*a* and 103*b* are arranged inside the sheath 21 that is a member for regulating the shape of the curved portion 84 of the nozzle 14, so that the lead wires 103*a* and 103*b* are covered by the sheath 21. Accordingly, the lead wires 103*a* and 103*b* can be rather easily and compactly wired along the nozzle 14.

When the sprayer 10 is used in a laparotomy, the color of the light emitted by the light source 102 may have a wavelength that is easily absorbed by the anti-adhesive material. In this case, since brightness of the irradiated site when viewed from the outside changes depending on an amount of application, an amount of the anti-adhesive material applied to the target site can be relatively easily known by using the brightness as an indication. This helps enable the anti-adhesive material to be uniformly applied along the suture portion 122 (can reduce uneven application), and can reduce the amount of anti-adhesive material used.

Figure 6:
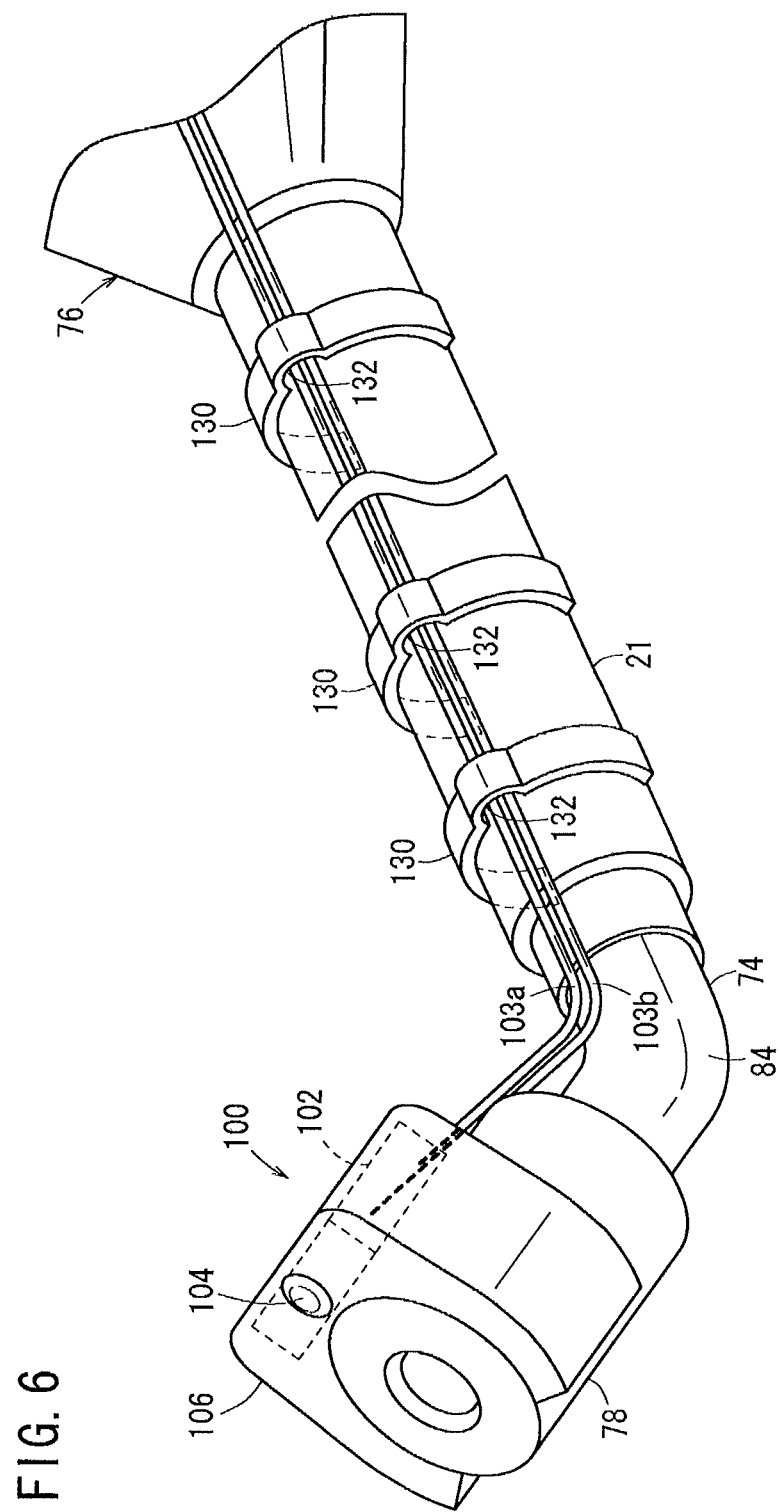
FIG. 6 is a partially omitted perspective view of a modified version of the sprayer including a wiring structure.

Instead of the above-described wiring structure in which the lead wires 103*a* and 103*b* are arranged to pass inside the sheath 21, there may be employed a wiring structure in which, like the sprayer 10 depicted in FIG. 6, the lead wires 103*a* and 103*b* are fixed to an outer periphery of the sheath 21 with a plurality of fixing devices 130 thereby to arrange the lead wires 103*a* and 103*b* along the nozzle 14. In this wiring structure, each of the fixing devices 130 has a shape of notching a part of a circle in an angle range smaller than 180 degrees, and includes a concave region 132 on the inner periphery of the fixing device 130 for receiving the lead wires 103*a* and 103*b*.

The fixing device 130 is elastically deformed thereby allowing spacing between both ends to be widened. In a natural state (a state without any external force applied), the spacing between both ends is smaller than an outer diameter of the sheath 21. Such a fixing device 130 can be made of various metals, alloys, resins and the like each having elasticity. The plurality of fixing devices 130 configured as describe above are mounted to the sheath 21 while the lead wires 103*a* and 103*b* are positioned in the concave 132 of each of the fixing devices 130, thereby integrally fixing the lead wires 103*a* and 103*b* to the outer periphery of the sheath 21.

Next, a sprayer 140 according to a second embodiment will be described below with reference to FIG. 7. Components in this second embodiment of the sprayer 140 that exert a function and an effect the same as or similar to those of the component in the sprayer 10 according to the first embodiment are designated by common reference numerals and a detailed description of such features will not be repeated.

Figure 7:
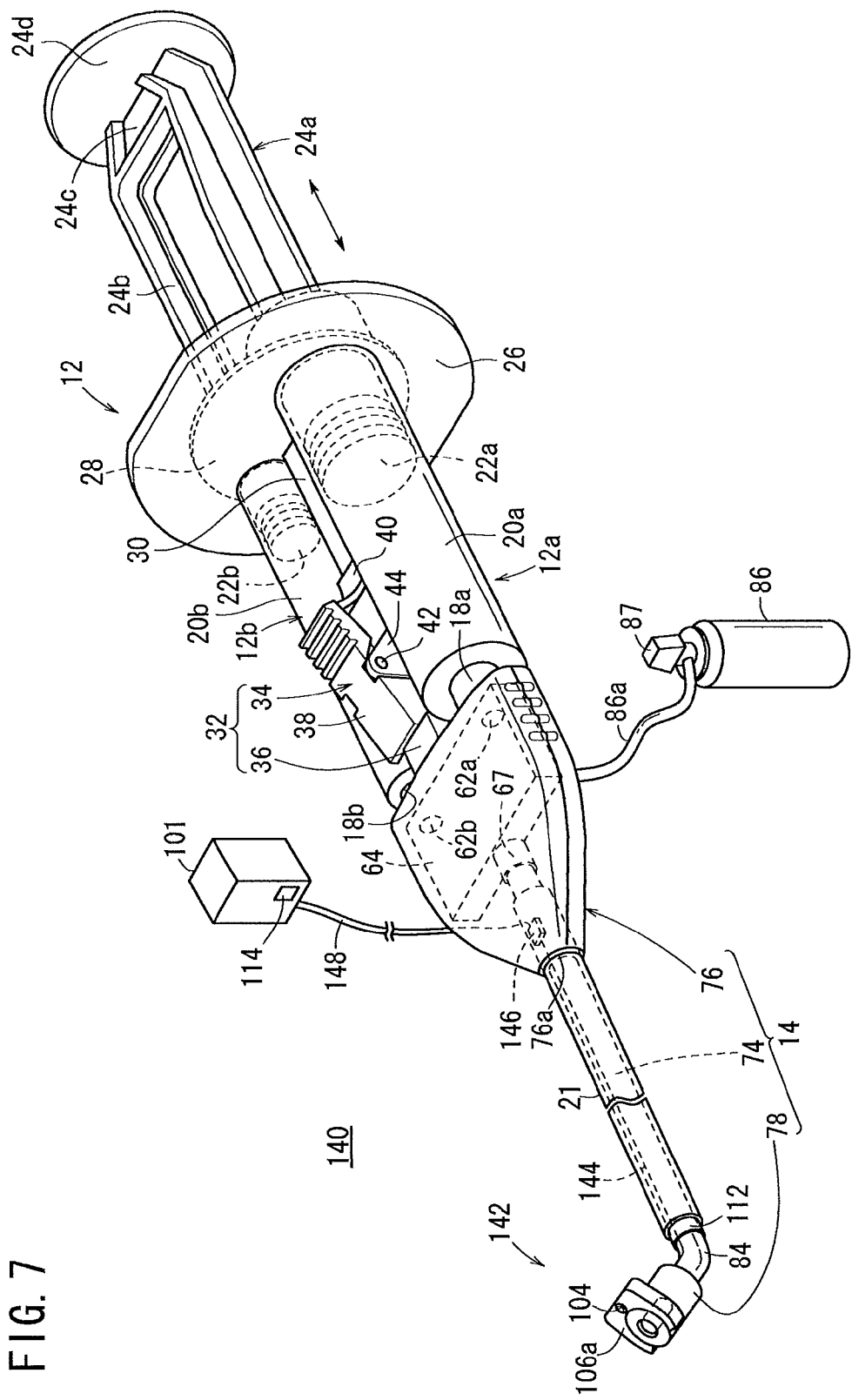
FIG. 7 is a partially omitted perspective view of a sprayer according to another embodiment disclosed here.

Instead of the irradiation unit 100 and the lead wires 103*a* and 103*b* associated with the first embodiment, the sprayer 140 according to the second embodiment depicted in FIG. 7 has an irradiation unit 142, an optical fiber (a light-guiding member) 144, and a light source 146. The irradiation unit 142 is structured by the lens 104. The lens 104 is held by a holding member 106*a* to be fixed to the nozzle head 78. That is, unlike the irradiation unit 100 in the first embodiment, the irradiation unit 142 in the second embodiment does not include a light source. Instead, the light source 146 is disposed in the nozzle support unit 76, and light emitted from this light source 146 is configured to be guided to the lens 104 through the optical fiber 144 arranged along the nozzle body 74. The holding member 106*a*, which does not hold or contain the light source 146, is smaller than the holding member 106 depicted in FIG. 2.

The light introduced to the lens 104 through the optical fiber 144 is transformed through the lens 104 into light (diffused light) that widens or diverges toward the end (in a direction away from the holding member 106*a*), and is irradiated in the leading end direction of the nozzle 14. The widening degree or degree of divergence of diffused light emitted from the irradiation unit 142 is set to be the same as that emitted from the irradiation unit 100 in the first embodiment.

The optical fiber 144 depicted in FIG. 7 is covered by the covering member 112 and arranged so as to pass inside the sheath 21, similar to the wiring structure of the lead wires 103*a* and 103*b* depicted in FIG. 2. However, instead of such a wiring structure, the optical fiber 144 may be fixed to the sheath 21 by the plurality of fixing devices 130 along the outer periphery of the sheath 21, similar to the wiring structure depicted in FIG. 6.

As the light source 102, a semiconductor laser, a light emitting diode, an electric bulb, and the like can be used. The light source 102 is electrically connected to the power source unit 101 via a cable 148. When the switch 114 of the power source unit 101 is turned on, electric power is supplied to the light source 102 to emit light. The light from the light source 102 is introduced to the lens 104 through the optical fiber 144, transformed through the lens 104 into diffused light, and irradiated in the leading end direction of the nozzle 14.

According to the sprayer 10 of the present embodiment, since the irradiation unit 142 emitting light that widens or diverges toward the end is provided at the leading end of the nozzle 14, the direction of the leading end of the nozzle 14 and the distance to the object can be known based on the position and the size (the diameter) of the light in the irradiated site. This allows the anti-adhesive material to be applied to an exact site.

Also, in the present embodiment, since the lens 104 is disposed to the leading end of the nozzle 14 and light is guided to the lens 104 by the optical fiber 144, the holding member 106a can be structured to be smaller compared to the holding member 106 in the first embodiment in which the light source 102 is disposed on the leading end of the nozzle 14. Thus, the leading end of the nozzle 14 can be constructed in a relatively compact manner.

The components in the second embodiment of the sprayer that are common with components in the first embodiment can exert a function and an effect that are the same as or similar to those exerted by the common component in the first embodiment and so a detailed description of such aspects will not be repeated.

The detailed description above describes several versions of a sprayer and manner of use or operation which are disclosed by way of example. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of applying a drug to a target site in a living body, the method comprising:
    inserting a leading end of a nozzle into a living body, the nozzle including a drug discharge port from which the drug is discharged, and an irradiation unit that emits light that diffuses in a direction away from the nozzle;
    irradiating tissue in the living body by directing the diffused light from the irradiation unit in a direction at the tissue;
    adjusting a position of the nozzle so that an irradiated site of the tissue that is irradiated by the diffused light is aligned with the target site;
    discharging the drug from the nozzle in a direction at the target site to apply the drug to the target site; and
    wherein the direction in which the diffused light is directed from the irradiation unit and the direction in which the drug is discharged from the nozzle are substantially the same so that a direction of orientation of the leading end of the nozzle at which the drug discharge port is located and from which the drug is discharged is predicted by visually observing the irradiated site.

2. The method according to claim 1, wherein the inserting of the leading end of the nozzle into the living body comprises inserting the leading end of the nozzle into a space between an organ and the tissue, and the irradiating of the tissue in the living body comprises irradiating the tissue from the back side of the tissue, and the adjusting of the position of the nozzle so that the irradiated site of the tissue irradiated by the diffused light is aligned with the target site comprises visually observing the irradiated site from a front side of the tissue.

3. A method of applying a drug to a target site of membranous tissue, the membranous tissue having a back side and a front side, wherein the front side of the membranous tissue is visually observable by a user, the method comprising:
    inserting a leading end of a nozzle into a living body, the nozzle including a drug discharge port from which the drug is discharged, and an irradiation unit that emits light that diffuses in a direction away from the nozzle, the leading end of the nozzle being inserted into the living body to position the drug discharge port and the irradiation unit on a back side of the membranous tissue;
    irradiating the membranous tissue by directing the diffused light from the irradiation unit at the back side of the membranous tissue;
    adjusting a position of the nozzle so that an irradiated site of the membranous tissue that is irradiated by the diffused light is aligned with the target site, the position of the nozzle being adjusted by visually observing, from the front side of the membranous tissue, the irradiated site; and
    discharging the drug from the nozzle at the target site to apply the drug to the target site.

4. The method according to claim 3, wherein the drug is an anti-adhesive material.

5. The method according to claim 3, wherein the membranous tissue is peritoneum in the living body, and wherein the inserting of the leading end of the nozzle into the living body to position the drug discharge port and the irradiation unit on the back side of the membranous tissue includes positioning the drug discharge port and the irradiation unit between the peritoneum and an organ in the living body.

6. The method according to claim 3, further comprising holding the membranous tissue with a gripper and holding-up the membranous tissue through use of the gripper so that the membranous tissue is spaced from an organ in the living body, and wherein the inserting of the leading end of the nozzle into the living body to position the drug discharge port and the irradiation unit on the back side of the membranous tissue includes positioning the drug discharge port and the irradiation unit between the membranous tissue and the organ.

7. The method according to claim 3, wherein the inserting of the leading end of the nozzle into the living body to position the drug discharge port and the irradiation unit on the back side of the membranous tissue includes inserting the leading end of the nozzle through a hole in an abdominal wall in the living body and into an abdominal cavity in the living body.

8. A method of applying a drug to a suture portion of tissue in a living body, the tissue having a back side and a front side, wherein the front side of the tissue is visually observable by a user, the method comprising:
    inserting a leading end of a nozzle into a living body, the nozzle including a drug discharge port from which the drug is discharged, and an irradiation unit that emits light that diffuses in a direction away from the nozzle, the leading end of the nozzle being inserted into the living body to position the drug discharge port and the irradiation unit on a back side of the tissue;
    irradiating the tissue by directing the diffused light from the irradiation unit at the back side of the tissue;
    adjusting a position of the nozzle so that an irradiated site irradiated by the diffused light is aligned with the suture portion, the position of the nozzle being adjusted by visually observing, from the front side of the tissue, the irradiated site; and
    discharging the drug from the nozzle at the suture portion to apply the drug to the back side of the suture portion.

9. The method according to claim 8, wherein the drug is an anti-adhesive material.

10. The method according to claim 8, wherein the tissue is peritoneum in the living body, and wherein the inserting of the leading end of the nozzle into the living body to position the drug discharge port and the irradiation unit on the back side of the tissue includes positioning the drug discharge port and the irradiation unit between the peritoneum and an organ in the living body.

11. The method according to claim 8, further comprising holding the tissue with a gripper and holding-up the tissue through use of the gripper so that the tissue is spaced from an organ in the living body, and wherein the inserting of the leading end of the nozzle into the living body to position the drug discharge port and the irradiation unit on a back side of the tissue includes positioning the drug discharge port and the irradiation unit between the tissue and the organ.

12. The method according to claim 8, wherein the inserting of the leading end of the nozzle into the living body to position the drug discharge port and the irradiation unit on a back side of the tissue includes inserting the leading end of the nozzle through a hole in an abdominal wall in the living body and into an abdominal cavity in the living body.

* * * * *